United States Patent [19]

Greenwood et al.

[11] 4,006,405
[45] Feb. 1, 1977

[54] METHOD AND APPARATUS FOR MEASURING PARAMETERS OF A CONDUCTIVE MATERIAL WHICH CAN BE USED IN INDEPENDENTLY DETERMINING THICKNESS AND CONDUCTIVITY

[75] Inventors: Ivan A. Greenwood, Stamford, Conn.; Donald S. Bayley, Bedford, N.Y.

[73] Assignee: The Singer Company, Little Falls, N.J.

[22] Filed: Jan. 13, 1975

[21] Appl. No.: 540,624

[52] U.S. Cl. .............................. 324/34 TK; 324/40
[51] Int. Cl.² .................................... G01R 33/12
[58] Field of Search ............... 324/34 R, 34 TK, 40

[56] References Cited

UNITED STATES PATENTS

| | | | |
|---|---|---|---|
| 3,693,075 | 9/1972 | Forster | 324/40 |
| 3,764,897 | 10/1973 | Greenwood | 324/40 |

FOREIGN PATENTS OR APPLICATIONS

| | | | |
|---|---|---|---|
| 593,956 | 10/1947 | United Kingdom | 324/34 TK |
| 260,189 | 8/1970 | U.S.S.R. | 324/34 TK |

OTHER PUBLICATIONS

Dodd, C. V., Applications of a Phase Sensitive E. C. Instrument Mat. Eval., June 1964, pp. 260–262 and 272.
McMaster, R., Nondestructive Testing Handbook, vol. II, The Ronald Press, 1963, pp. 39.12–39.19.

*Primary Examiner*—Robert J. Corcoran
*Attorney, Agent, or Firm*—Thomas W. Kennedy

[57] ABSTRACT

A method and apparatus for making measurements of an electrically conductive material, which measurements can be used to determine the separate parameters thickness and conductivity without knowledge of the value of either of these parameters and in a manner giving improved freedom from sheet flutter, in which a transmitter coil is placed on one side of the sheet of material to be measured and a receiver coil on the other side at fixed distance from the transmitter coil and the transmitter coil is operated at two separate frequencies to obtain two relative phase relationships between the current in the transmitter coil and the electromotive force in the receiver coil such that the resulting phases differ in their functional relationships to thickness and conductivity, the frequency and phase being measured to obtain values which then can be used in independent equations to solve for at least one of thickness and conductivity.

9 Claims, 6 Drawing Figures

METHOD AND APPARATUS FOR MEASURING PARAMETERS OF A CONDUCTIVE MATERIAL WHICH CAN BE USED IN INDEPENDENTLY DETERMINING THICKNESS AND CONDUCTIVITY

BACKGROUND OF THE INVENTION

This invention relates to electromagnetic thickness measurements in general, and more particularly to an improved method and apparatus for measuring the thickness of metal sheets.

It is well known in the art that the phase of an electric field resulting from eddy currents induced in a conducting sheet by a transmitter will have a phase relationship to the phase of the transmitter which is a function of the conductivity and the thickness of the conducting sheet. Various thickness gauges have been developed based on this principle. The simplest gauges developed for this purpose suffered from two deficiencies. First, they were only operable with sheets of known conductivity. That is, since the phase shift is a function of both conductivity and thickness, conductivity needed to be known in order to relate thickness and phase shift. Secondly, these gauges were unduly sensitive to the distance of transmitting and receiving coils from the conducting sheet being gauged. That is, the phase angle varied with the distance. Thus, they were impractical for measuring thickness of sheet metal as it was being manufactured because of the considerable transverse movement of the metal sheet making it impossible to maintain constant distances between the sheet and transmitting and receiving coils. Furthermore, in this type of application, the conductivity of the sheet tends to vary thereby further adding to the difficulty of making measurements.

An apparatus and method for solving this problem is disclosed in U.S. Pat. No. 3,764,897. In the electromagnetic thickness gauge disclosed therein, dependence on the distance of the coil from the sheet being gauged is eliminated through the use of a transmitting coil designed so as to generate a magnetic field so shaped that the phase angle of the sensed field due to the induced eddy current is substantially invarient with the distance between the metal sheet and the coil. To overcome the problem of conductivity, two eddy current measurements in which the phase angle varies in a different manner with variation in thickness and conductivity are taken. Thus, by solving simultaneous equations relating to these two phase angles, it is possible to determine both thickness and conductivity. A number of embodiments are shown, each in which a first measurement is made at a relatively low frequency where the phase angle is proportional to the inverse of the product of the conductivity and thickness with a second measurement made at a high frequency which the phase angle proportional to the square root of the conductivity. In each of the embodiments disclosed and illustrated, at least one measurement is a reflectance measurement.

Although the method and apparatus described therein works quite well, it suffers from a number of deficiencies which although not fundamental to its operations are of great practical importance. In particular, the signal to noise ratio required is very difficult to achieve in view of the following:

a. the necessity for balancing out signals from the transmitter;

b. the requirements for high values of $q$ to obtain adequate phase shift;

c. the requirement for sufficient separation between the sheet and transducer to accomodate normal flutter and other tolerances in the sheet position. Furthermore, a specially designed coil of complex construction is required. In view of this, it is clear that there is need for an improved method and apparatus for making thickness measurement which does not suffer from these deficiencies.

SUMMARY OF THE INVENTION

The present invention provides such a method and apparatus. It makes use of a two frequency approach similar to that of the above cited patent but rather than using reflectance measurements, makes two transmission measurements. This results in several important and favorable consequences as follows:

a. the signal to noise ratio is very good and is not subjected to the requirement of bridge balancing;

b. since the distance between the transmitter and receiver coils is constant, a design providing a constant mode parameter $q$ over a range of separations is not required and simple coils can be used;

c. the sensitivity in terms of the size of the angle sensed is good;

d. measurements may be taken at lower frequencies; and e. the method may be carried out with considerably lower values of $q$ than are necessary for making reflectance measurements and as a result much larger coils spaced further apart can be used.

In its broadest terms, the present invention comprises making phase measurements at two frequencies using either duplicate sets of apparatus or a single apparatus including means to produce and separate the two frequencies. Because the relationship between phase angle conductivity and thickness is different at different frequencies, this permits solving in a completely general way for thickness and conductivity. For a solution to have optimum convergence, one measurement should preferably be made in or at least near a region where the sheet is thin compared to the skin depth of the eddy currents and the other measurement in a region where the thickness approaches the skin depth.

Although the present invention can be practiced by using constant frequencies and measuring phase angle it is preferred that predetermined phase angle values be established and the frequencies then varied to obtain these phase angles. It becomes particularly simple to implement the method of the present invention if one phase angle is selected as 90° and a second phase angle selected near 16°. With this arrangement, thickness can be derived from the ratio of the resulting frequencies in accordance with the equations below where $l$ is thickness and $\sigma$ is conductivity.

$$l = 3\omega_2{}^2(\omega_1{}^2q \tan {}^2\phi_2),$$

$$\sigma = (2\omega_1{}^2q^2\tan^3\phi_2) / (3\omega_2{}^3\mu_o)$$

In these equations, $\omega_1$ is the frequency for which the transmitted phase lag has a first predetermined value of 90°, $\omega_2$ is the frequency for which the transmitted phase angle has the second predetermined value near 16°, and $q$ is the effective mode parameter described in detail in the above references U.S. patents and $\mu_o$ is the permeability of free space. As will be disclosed in detail below, $q$ may be determined experimentally from the slope of the response magnitude versus distance between coils at the coil separation used.

A first embodiment in which the system is operated in an open loop manner and precision phase measurement made is illustrated. In this embodiment, an oscillator through appropriate drivers drives a transmitting coil to induce eddy currents in the sheet being gauged and a pickup coil provided as a receiver. Comparison is made between the transmitter phase and the receiver phase to determine the phase shift caused by the eddy currents. By alternately operating the apparatus at different frequencies the two required measurements are made.

In the preferred embodiment, a self-oscillating circuit which operates at a frequency for which the phase shift around the loop is zero is provided. In this embodiment, the transmitter is driven by a coil driver having an input from a main amplifier which has for its input the output of a preamplifier associated with the receiving coil. In general terms, a phase shift is provided within the loop so that the loop will adjust itself until the phase shift caused by the sheet just cancels the phase shift preset into the loop. The nature of the apparatus is such that with no sheet interposed between the transmitter and receiver, the voltage picked up by the pick-up coil will be in time quadrature with the input voltage. More specifically, it will lead by 90°. With no additional phase shift introduced into the loop and with a metal sheet inserted, a 90° lag at a particular frequency will result in an overall zero phase shift. Thus, the loop will oscillate at a frequency corresponding to a 90° phase shift, i.e., a 90° lag caused by the sheet being gauged. If for the second measurement a phase shift, for example, the 16° phase shift or 16° lag noted above is desired, then an additional lag must be introduced into the loop, i.e., in this example a 74° lag. With such a lag in the loop the frequency will then be that frequency at which a 16° phase shift lag is introduced by the sheet being gauged. Thus, in a simple manner, two frequencies may be determined and used in the above equations to determine thickness and conductivity.

Various details of the circuits used are disclosed along with calibration methods and alternate embodiments of the invention.

DETAILED DESCRIPTION OF THE PREFERRED EMBODIMENT

Figure 1:
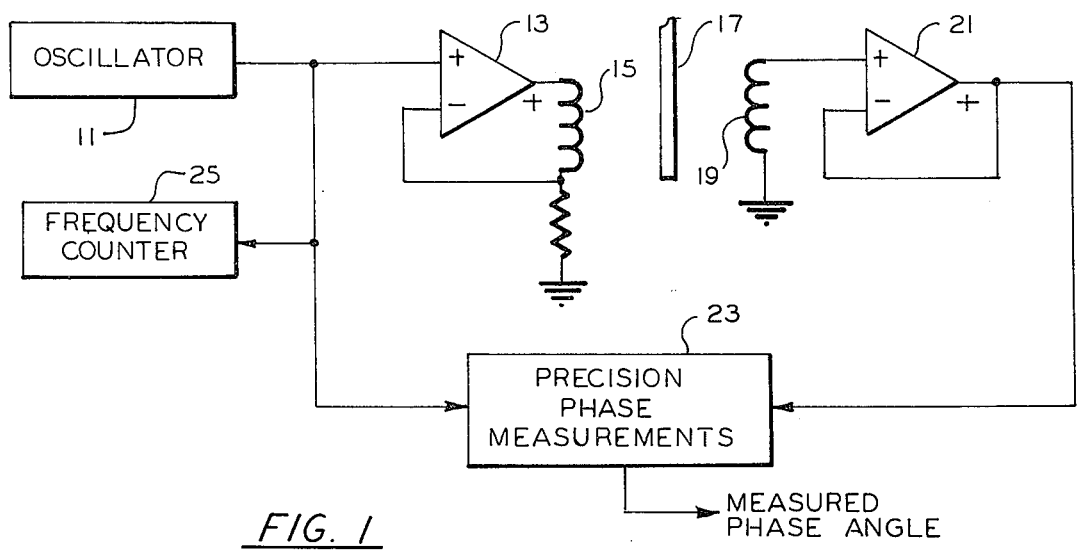
FIG. 1 is a block-schematic diagram of a system according to the present invention making open loop phase measurements.

The above referenced U.S. patent goes into some detail regarding the basic theory of the effects of eddy currents on signals reflected from and transmitted through a conducting sheet. The theory on which the present invention is based is identical. For a fuller understanding of the present invention, a summary of that theory will now be given.

A solution of Maxwell's equation in cylindrical coordinates, $z$, $r$, and $l$, shows that the magnetic field of a transmitter which is symmetrical around the $z$ axis can be expressed as a summation of single-mode fields. In particular, for the single-mode $z$ component whose separation parameter is $q$, the magnetic field for $r=0$ is given by:

$$H = H_o \exp(j\omega t)\exp(-qz), \tag{1}$$

where $\omega$ is the angular frequency of the transmitter excitation, and $H_o$ and $H$ are the complex amplitudes of the single mode at the transmitter and at a distance $z$ away.

The solution also shows that for a sheet of thickness $l$, conductivity $\sigma$, and relative permeability $\mu = 1$, the complex reflectivity R and complex transmissivity T are given by $$R = \frac{(\alpha - \beta)\sinh \gamma l}{\cosh \gamma l + (\alpha + \beta)\sinh \gamma l}, \tag{2}$$

and $$T = \frac{1}{\cosh \gamma l + (\alpha + \beta)\sinh \gamma l}, \tag{3}$$

where, $\alpha = \gamma/(2q), \beta = 1/(4\alpha)$ $\gamma = +(q^2 + jQ^2)^{1/2}$, $Q^2 = \omega\mu_0\sigma\mu$, and the permeability of free space $\mu_o = 4\pi \times 10^{-7}$ henry/meter.

For the reflection measurements single mode transmitters and receivers are required. In these measurements the signal is measured by a pick-up coil arrangement located at the transmitter. If the sheet is at a distance $z_S$ away, then for each mode the pick-up senses a magnetic field $H_R$ given from equation (1) by $$H_R = RH_o\exp(j\omega t)\exp(-2qz_S). \tag{4}$$

Equation (2) shows that the phase of the reflectivity depends on the value of the single-mode parameter $q$ and equation (4) shows that the free-spaced attenuation of the signal depends on both $q$ and the sheet position $z_S$. If more than one mode is present the phase of the resultant signal, given by summing over all modes, must therefore change whenever the sheet is moved.

It is for this reason that single-mode probes must be used to prevent sheet flutter from affecting the measurement of the reflectance phase angle. As described below single-mode probes are not so required for phase measurements with transmitted signals.

For the transmission measurements a receiver coil is located at a distance $z_T$ away from the other side of the sheet. The single mode magnetic field component $H_T$ at the pick-up coil is $$H_T = TH_o\exp(j\omega t)\exp[-2q(z_S+z_T)]. \tag{5}$$

Since $z_S+z_T$ equals the transmitter-receiver spacing minus the sheet thickness $l$, it now remains constant when the sheet is displaced. Consequently, the attenuation factor, exp $[-2q(z_S+z_T)]$ no longer depends on sheet position, and both the amplitude and phase of the single-mode receiver signal $H_T$ will now remain constant when the sheet is displaced. Since this independence must exist for any other mode defined by a different value of $q$ it must also exist as regards the amplitude and phase of the total receiver signal resulting from the summation over these orthogonal modes.

Transmission measurements can therefore be performed in multi-mode fields and the resulting determination of thickness and conductivity will be independent of the location of the sheet between the transmitter and receiver. As a result the transmitter and receiver can be single coils. There is no longer a need for the coil arrays necessary in the reflection measurements.

A rigorous theoretical description of the operation in multi-mode fields would require summing the single mode components described above over a spectrum of mode parameter values determined by analysis of the magnetic field produced by transmitter coil and the effective field at the receiver coil. However, it will be assumed instead that the single mode equations will remain valid if an effective value of the mode parameter $q$ can be determined either by calibration or other means. It will be seen below that this simplification provides an excellent tool for analyzing the measurements.

The determination of thickness and conductivity from transmissivity measurements can be simplified by using an accurate approximation, rather than equation (5), for determining the transmissivity phase angle $\phi_T$. This approximation is based on the series expansions for tanh $x$ and tan $x$. Derivation shows that, where $\phi_T'$ is that approximate phase lag, $$\tan \phi_T' = 6l\omega\mu_o\sigma(12q-l^3\omega^2\mu_o^2\sigma^2)^{-1}. \quad (6)$$

Comparative computations using equation (6) and equation (3) have shown that the values obtained for phase lag over frequencies from one to more than 25 kilohertz have variations which in practical terms are negligible.

With the basic theory described above in mind, the theory upon which the apparatus of the present invention is based will now be explained.

In equation (6) the coefficients of the two frequency dependent terms are different functions of thickness and conductivity. A measurement of the phase lag at a high frequency $\omega_1$ will emphasize the dependence of $\phi_T'$ on $l^2\sigma$, while that at a much lower frequency $\omega_2$ will emphasize the $l\sigma$ product. The actual procedure for determining $l$ and $\sigma$ from such measurements is described below. Here a simplified case will be used to illustrate the method.

Equation (6) shows that a high frequency $\omega_1$ can be chosen so that the phase lag is 90°, which occurs when $$\omega_1^2 l^3 \mu_o^2 \sigma^2 = 12q. \quad (7)$$

At a second frequency $\omega_2$, small enough that $$\omega_2^2 l^3 \mu_o^2 \sigma^2 << 12q,$$

equation (6) shows that $$\omega_2 l \mu_o \sigma \sim 2q\tan\phi_2, \quad (8)$$

where $\phi_2$ is the correspondingly smaller phase lag. Solving equations (7) and (8) for $l$ and $\sigma$ gives $$l = 3\omega_2^2/(\omega_1^2 q \tan^2\phi_2), \quad (9)$$

and $$\sigma = (2\omega_1^2 q^2 \tan^3\phi_2)/(3\omega_2^3 \mu_o). \quad (10)$$

There are two basic arrangements for making the required measurements, namely, open or closed-loop circuitry. In both arrangements either two transmitters and two receivers in order to permit simultaneous measurements at the frequencies $\omega_1$ and $\omega_2$ or, alternatively, a single transmitter-receiver and suitable filters could be used. FIG. 1 illustrates in block diagram form a transmitter receiver arrangement for making open loop phase measurement. One such apparatus is shown which may be alternately operated at the different required frequencies or may be duplicated so that both measurements may be made at the same time. The apparatus comprises an oscillator 11 having its output coupled to an amplifier 13 driving a transmitter coil 15. As illustrated the transmitter is placed on one side of the sheet 17 to be gauged with a pickup coil 19 on the other side. The signal received by the pickup coil is provided to a buffer amplifier 21. The output of this amplifier along with the output of oscillator 11 are provided to a precision phase meter 23 where the phase angle difference is measured. Also shown is a frequency counter 25. In operating apparatus of this nature, the frequency of the oscillator 11 is adjusted until the measured phase angle is for example 90° and the frequency at which this phase shift occurs obtained from the frequency counter. With the same or separate identical apparatus, the oscillator is adjusted to obtain a second smaller phase angle i.e., phase lag of for example, 10° to 20° and the frequency again obtained. This information may then be used along with calibration data to obtain values of thickness and conductivity in accordance with equations (9) and (10) above.

Figure 2:
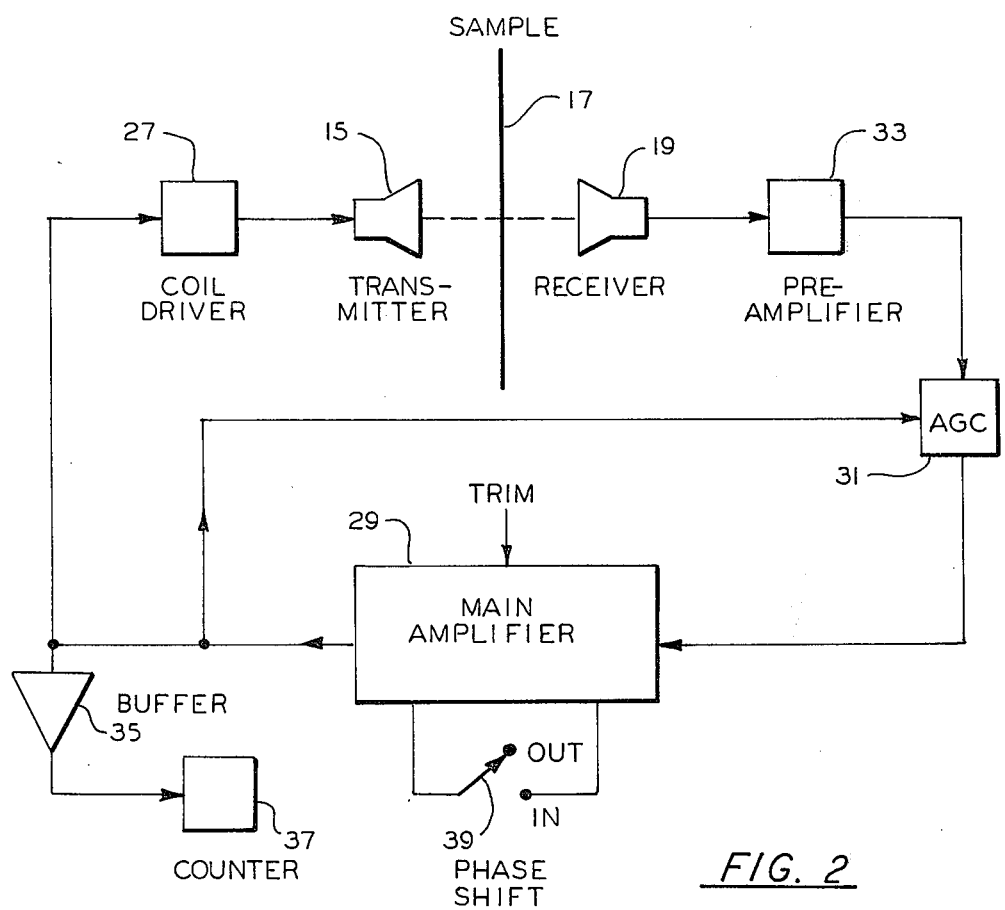
FIG. 2 is a similar diagram illustrating a closed loop phase shift system.

In the preferred embodiment however, rather than using an open loop system, a closed loop feedback arrangement such as that shown in FIG. 2 is used. Here, the sample or sheet 17 is again placed between a transmitting coil 15 and a receiving coil 19. The transmitting coil is driven by a coil driver 27 which obtains its input from a main amplifier 29. The input to amplifier 29 is from an automatic gain control circuit 31 with the automatic gain control circuit input being provided by preamplifier 33 which is coupled to the output of the receiver coil 19. Without any phase shift introduced by a sample sheet 17, the system will of nature have a 90° phase lead. As a result, if no further phase shift is introduced into the loop, the loop will oscillate at a frequency such that the phase shift through the loop is 0. This will require a 90° phase lag introduced by the sample sheet 17. Thus, a first frequency which results in a 90° phase lag caused by the material being gauged can be accomplished in a simple manner. The output of the main amplifier 29 which will be at this frequency is provided to a buffer amplifier 35 to a frequency counter 37 so that frequency can be obtained as an output. In the illustrated embodiment, the main amplifier is provided with a switch 39 to permit switching into the loop an additional phase shift. For example, a phase lag of 74° can be introduced through closing this switch. Now only 16° of phase lag must be made up by a phase shift in the sheet being gauged, and the system will now oscillate at a frequency which provides such a phase shift. This frequency can then also be measured by the counter 37. With these two frequencies and calibration data relating to the value $q$ and possibly the phase angle $\phi_2$ available, the thickness and conductivity can be obtained from equations (9) and (10).

One of the important requirements for the thickness gauge is the use of coils with low inductance and distributed capacities so that their resonant frequencies are large compared with the highest frequency of system operation. A high frequency roll off can then be introduced to suppress closed loop oscillation near the coil resonance without appreciably affecting the phase shift at the operating frequency. The low inductance transmitter coil must then be driven at a high current level in order to obtain sufficient closed loop gain with thick samples and large transmitter-receiver separation. Preferably the coils used in this instrumentation have resonant frequencies at about 4 MHz. They can be identical, with each, for example, a flat spiral of 55 turns of No. 32 cloth and enamel covered copper wire. Typical dimensions are an outside diameter of 2 inches and inside diameter of one-half inch. Deformation can be prevented by cementing each coil to a lucite backing plate. A schematic of the coil driver is illustrated on FIG. 3. The output from the main amplifier is coupled through a capacitor C1 into an emitter follower stage including transistor T1. The coil 15 is energized by the collector current of transistor T1 to insure good accuracy i.e. coil current rather than voltage is controlled by the input signal. Such precise current control is implied in the analysis above which predicts that measurement will be independent of sample position. Without good control of the current in the coil, the eddy currents in the sheet will induce position dependent changes in the transmitter coil current and hence in the magnetic field $H_0$ which was assumed constant in this analysis above. As illustrated, the remainder of the coil driver circuit comprises a voltage divider made up of resistances R1 and R2 across the positive and negative voltage establishing a bias at the base input to transistor T1 with two parallel emitter resistors R3 and R4 coupling the emitter to the negative voltage. As shown, the transmitting coil 15 is coupled to the collector with its other side coupled through a resistor R5 and capacitor C2 in parallel to the positive voltage supply. The emitter is also coupled through a resistor R6 to a monitor point.

Experiments have indicated that placing a small capacitor or large resistor in parallel with the coil violates the constant current requirement. Under these conditions, displacement of this sample sheet resulted in changes of amplitude of the receiver signal and changes in phase implied from associated changes in closed loop frequencies. It should also be noted that an unwanted influence of sample position will be introduced by coils wound on ferrite cores. Basically the requirement is that free space be simulated.

Figures 3, 4:
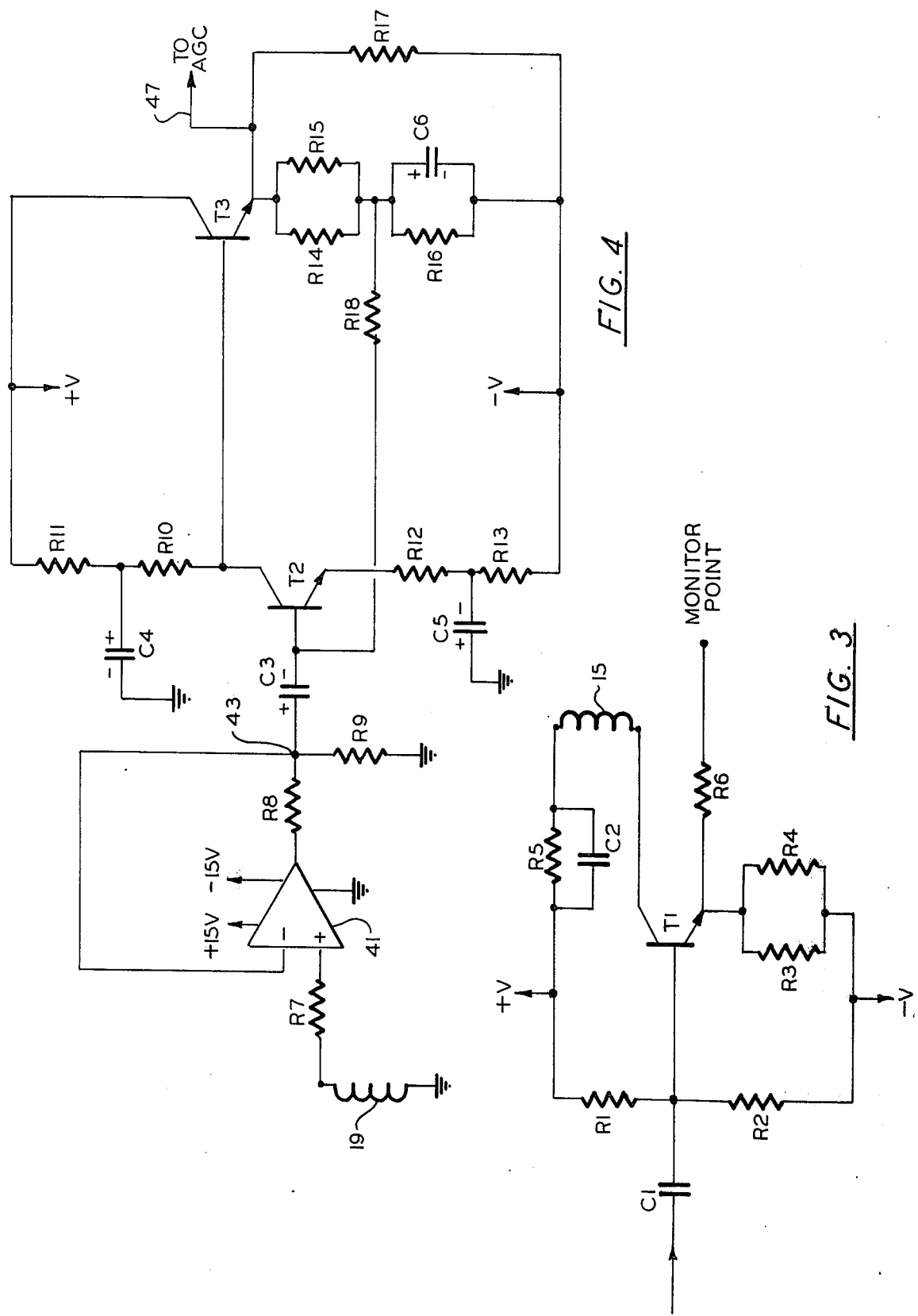
FIG. 3 is a schematic diagram of the coil driver of FIG. 2.
FIG. 4 is a schematic diagram of the preamplifier of FIG. 2.
Figure 5:
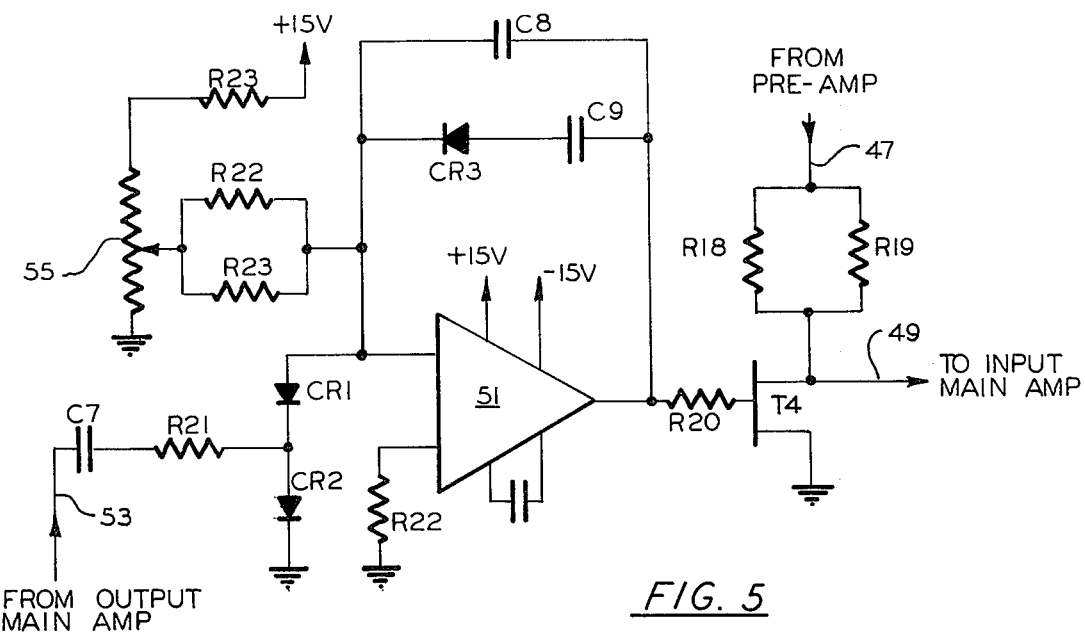
FIG. 5 is a schematic diagram of the automatic gain control of FIG. 2.
Figure 6:
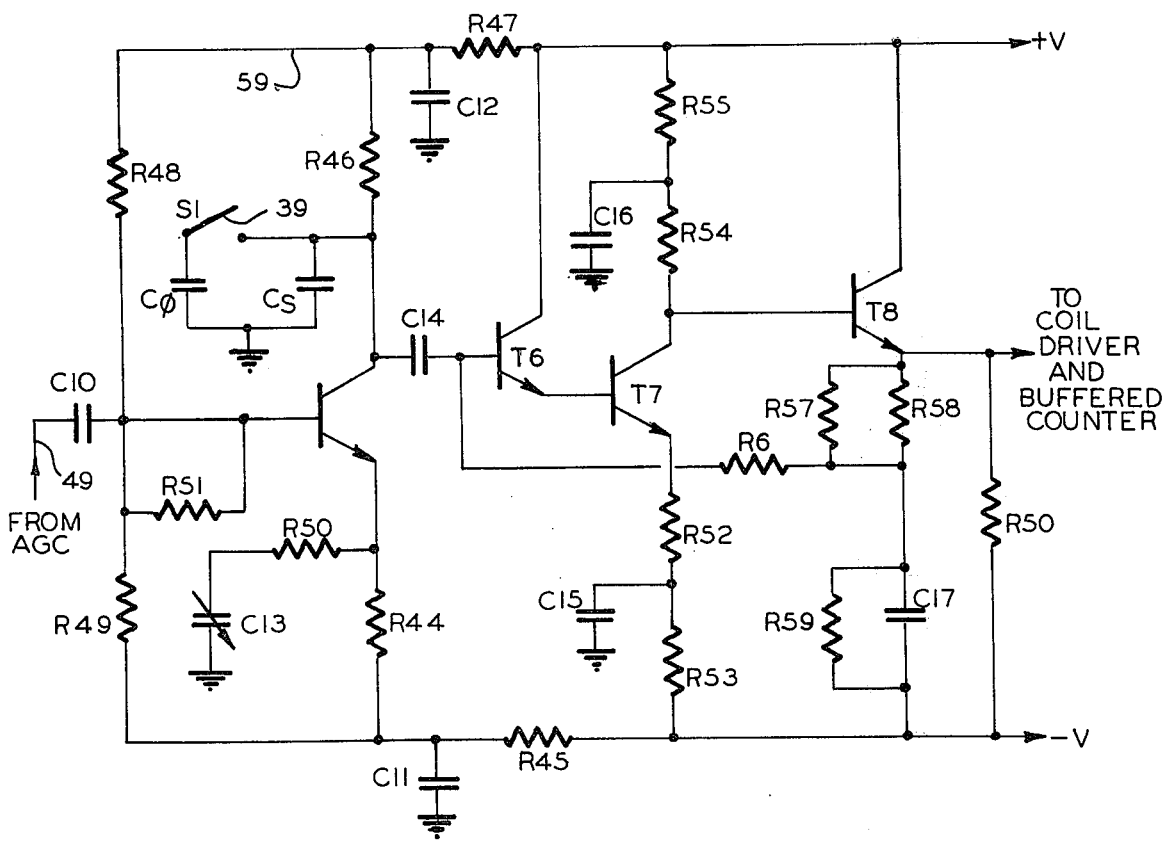
FIG. 6 is a schematic diagram of the main amplifier of FIG. 2.

With the above described coil driver, sufficient power is provided to allow operation at a receiver transmitter spacing of approximately one-half inch for measuring an aluminum sample that is 20 mils thick and has 42% ICAS conductivity. Operation with thicker sheets and larger spacings is of course, possible, using a more powerful driver with larger coils and heavier wires along with additional gain in the amplifiers. Typical components for use in the coil driver of FIG. 3 are as follows:

T1-2N2219A transistor
C1-1 $\mu$F
C2-100 $\mu$F
R1-5.1K
R2-10K
R3, R-180 ohms
R5-47 ohms
R6-100 ohms In this and other circuits ±15 volt supplies are normally used for the positive and negative voltages. A schematic diagram of the preamplifier 33 of FIG. 2 is shown on FIG. 4. The output of coil 19 is provided through a resistor R7 to the non-inverting input of buffer amplifier 41. The amplifier output is coupled through a resistor R8 to an output point 43 grounded through a resistor R9. Point 43 is fed back to the inverting input of amplifier 41. This results in a unity gain stage of amplification to minimize current in the coil 19 and to thereby minimize effects of sample displacement. The output at point 43 is coupled through a capacitor coupled to a further stage of amplification having a gain of about 10. Capacitor C3 provides an input to the base of a transistor T2 having its collector coupled through series resistors R10 and R11 to the positive voltage supply and its emitter coupled through resistors R12 and R13 in series to the negative voltage supply. The junctions of resistors R10 and R11 and R12 and R13 are decoupled respectively by capacitors C4 and C5 connected to ground. The collector output of transistor T2 is provided into the base of a transistor T3 having its collector coupled directly to the positive voltage supply and its emitter coupled through resistors R14 and R15 in parallel with that parallel combination in series with a resistor R16 and capacitor C6 to the negative voltage. The emitter is also coupled through a resistor R17 to the negative voltage terminal. Bias for the base of transistor T2 is provided through a resistor R18 connecting the junction point of the parallel combination of resistor R14 and resistor R15 with the parallel combination of resistor R16 and capacitor C6. As indicated, the output of the preamplifier on line 47 is provided to the automatic gain control. In this stage, transistor T2 and its associated circuitry results in a gain of approximately 10 with transistor T3 acting as an emitter follower to buffer the output. Typical components in the preamplifier of FIG. 4 are as follows:

Amplifier 41 - Intech A-148
C 4 - C 5 - 100 $\mu$F
C 4 - C 5 C 6 - 100 $\mu$F
R7 - 10 K
R8 - 91 ohms
R9 - 51 K
R14, R10 - 5· 6K
R13, R11 - 110 ohms
R16, R12 - 510 ohms
R15 - 6.8 K
R17 - 2K The automatic gain control 31 of FIG. 2 is shown in the schematic diagram of FIG. 5. The input on line 47 from the preamplifier is provided through resistors R18 and R19 to the source of a FET T4 the drain of which is coupled to ground. As illustrated, the output line of the circuit to the main amplifier 29 of FIG. 2 and designated 49 is from the source of FET T4. FET T4 has its gate connection coupled through a resistor R20 to the output of an operational amplifier 51. The output from the main amplifier of FIG. 2 on line 53 is coupled through a capacitor C7 and resistor R21 to the junction of two diodes CR1 and CR2 coupling the inverting input of amplifier 51 to ground. The non-inverting input terminal of amplifier 51 is coupled to ground through resistor 22. The operational amplifier is connected as an integrator with feedback provided from its output to its inverting input through a capacitor C8 in parallel with the capacitor C9 and diode CR3. This provides the necessary smoothing and single time constant required for good stability. The diodes at the input of the integrator allow the average current produced during approximately one-half cycle of the capacitive coupled output from the main amplifier to be balanced against current provided from a gain adjust potentiometer 55 which is providing an input through resistors R22 and R23 in parallel to the inverting input of amplifier 51. As illustrated the gain adjust potentiometer 55 is coupled on one end to ground and on the other end through a resistor R33 to the positive voltage. The main amplifier is shown on FIG. 6. Two gain stages are provided, each having a gain of 10 with interstage and output buffering provided by emitter followers. The input on line 49 from the automatic gain control is capacitive coupled to the first amplifier transistor T5. T5 has its emitter coupled through a resistor R24 to a negative voltage line 57 decoupled from the negative power supply by a resistor R45 and capacitor C11 to ground. Similarly, the collector of transistor T5 is coupled through a resistor R45 to a positive voltage line 59 decoupled by resistor R47 and capacitor C12 to ground. Biased at the base of transistor T5 is established by resistors R48 and R49 in series across lines 57 and 59. Also coupled to the emitter is a series circuit comprising a resistor R50 and trim capacitor C13 to ground. Capacitor C13 is provided to compensate as well as possible for any undesired phase lags in the electronics. Coupled to the collector of transistor T5 is a capacitor $C_s$ to ground and through the switch 39 a capacitor $C_\phi$ also to ground. Capacitor $C_s$ is required to suppress closed loop oscillations near coil resonance. Capacitor $C_\phi$ along with the switch 39 provide the phase shift control. With switch 39 open, the system will operate at the high frequency $\omega_1$. With it closed, the frequency is reduced to $\omega_2$. The output at the collector of transistor T5 is coupled through capacitor C14 to the base of an emitter follower transistor T6 having its collector coupled to the positive voltage and its emitter coupled to the base of a transistor T7 providing the second stage of amplification. Transistor T7 has its emitter coupled through a resistor R52 and R53 to the negative voltage. The junction of resistors R52 and R53 is decoupled to ground through a capacitor C15. The collector of transistor T7 is coupled through resistors R54 and R55 to the positive voltage with the junctions of these resistors similarly decoupled to ground through a capacitor C16. The collector output of transistor T7 is coupled to the base input of an emitter follower stage comprising transistor T8 and its associated circuitry. Transistor T8 has its collector coupled to the positive voltage and its emitter coupled through a resistor R56 to the negative voltage. In parallel with resistor R56 and also coupling the emitter to the negative voltage is a series circuit made up of parallel resistors R57 and R58 in series with a resistor R59 in parallel with a capacitor C17. Feedback from the junction of these two parallel combinations is provided through a resistor R60 to the base of the emitter follower T6. This negative feedback for the last stage maintains a bias which is stable and permits maintaining a large and undistorted voltage swing. The by-pass capacitor C17 maintains the AC again.

The operation of the measuring arrangement of FIG. 2 and its use in making thickness and conductivity measurements will now be explained in greater detail. As described above, it is proposed to operate this system with a phase lead of 90° for one measurement and a smaller phase lead $\phi_2$ for example between 10° and 20° for a second measurement, the respective phase leads causing oscillation at frequency $\omega_1$ and $\omega_2$ to cause corresponding phase lags in the sample sheet. It was further pointed out that the required phase lead of 90° is built into the system. It occurs in the receiver coil whose voltage output leads the magnetic field by 90°. If there are no other phase shifts the system will oscillate at the frequency $\omega_1$ corresponding to a 90° phase lag in the sample sheet. The phase lead $\phi_2$ must therefore be produced by reducing the built-in 90° lead with an introduced phase lag $\phi_L$, i.e. by closing switch 39.

In general then, the total phase shift around the loop will be zero and oscillation will occur when the sum of the phase lag $\phi_T$ in the sample sheet and the introduced phase lag $\phi_L$ equals 90°, i.e., when $$\tan\phi_T \tan\phi_L = 1. \tag{11}$$

It will now be assumed for the high frequency measurement that the capacitor C13 has been adjusted so that the residual phase lag $\phi_o$ in the electronics is very small and can be expressed as $$\tan\phi_o = \omega_1 \tau_1. \tag{12}$$

For the low frequency measurement when the capacitor C is connected by closing the switch $S_1$, it will be assumed that the corresponding phase lag is given by $$\tan \phi_L = \omega_2(\tau_2+\tau_1). \tag{13}$$

Combining the above equations with the approximation for $\phi_T$ represented by equation (6) then gives two simultaneous equations which determine the thickness and conductivity. These are $$12q = \omega_1{}^2 l\mu_o\sigma(l^2\mu_o\sigma+6\pi_1), \tag{14}$$

and $$12q = \omega_2{}^2 l\mu_o\sigma(l+2\mu_o\sigma+6\tau_1 30\ 6\tau_2). \tag{15}$$

Solving for $l$ and $\sigma$ gives $$l = 3\omega_1{}^2\tau_3(\tau_3-\tau_1)/q, \tag{16}$$

and $$\sigma = 2q^2/[3\mu_o\omega_1{}^4\tau_3{}^2(\tau_3-\tau_1)], \tag{17}$$

where $$\tau_3 = a\tau_2/(1-a), \tag{18}$$

and $$a = \omega_2{}^2/\omega_1{}^2. \tag{19}$$

The accuracy of this description of system operation will depend on the validity of the assumptions upon which the above analysis is based. To summarize, these are:

a. The phase lag $\phi_T$ can be determined from the approximate equation (6) above.

b. The frequency response of the electronic components over the region of operation is such that the time constants $\tau_1$ and $\tau_2$ are independent of frequency as required by the use of equations (12) and (13) to describe the residual and introduced phase lags.

c. The effective values of the time constants $\tau_1$ and $\tau_2$ as well as that of the single mode parameter $q$ can be determined by calibration of the system using samples of known properties.

The procedure for initial calibration of the system is based on the approximate analysis above except for the additional assumption that the effective value of the single mode parameter $q$ may depend slightly on thickness of the sample. Two sample sheets of known conductivity and thickness are used and the high and low closed loop frequencies are measured for each.

For the first sample of thickness $l_1$ and conductivity $\sigma_1$, the high and low frequencies will be designated by $\omega_{11}$ and $\omega_{12}$, respectively. The single mode parameter will be represented by $q_1$. For the second sample the corresponding symbols will be $l_2$, $\sigma_2$, $\omega_{21}$, $\omega_{22}$, and $q_2$.

For the first sample equations (16) and (17) require that $$12q_1 = l_1\omega_{11}^2\mu_0\sigma_1(l_1^2\mu_0\sigma_1+6\tau_1), \quad (20)$$

and $$12q_1 = l_1\omega_{12}^2\mu_0\sigma_1(l_1^2\mu_0\sigma_1+6\tau_2+6\tau_1). \quad (21)$$

Similarly, for the second sheet, $$12q_2 = l_2\omega_{21}^2\mu_0\sigma_2(l_2^2\mu_0\sigma_2+6\tau_1), \quad (22)$$

and $$12q_2 = l_2\omega_{22}^2\mu_0\sigma_2(l_2^2\mu_0\sigma_2+6\tau_2+6\tau_1). \quad (23)$$

Solving for the four parameters then gives $$\tau_1 = [a(b-c)T_2 - c(1-a)T_1]/(6D), \quad (24)$$

$$\tau_2 = (1-a)(b-c)(T_2-T_1)/(6D), \quad (25)$$

and $$q_1 = \omega_{11}^2 a(b-c)T_1(T_2-T_1)/(12Dl_1), \quad (26)$$

$$q_2 = \omega_{11}^2 bc(1-a)T_2(T_2-T_1)/(12Dl_2), \quad (27)$$

where $$T_1 = l_1^2\mu_0\sigma_1, \quad (28)$$

$$T_2 = l_2^2\mu_0\sigma_2, \quad (29)$$

$$a = \omega_{12}^2/\omega_{11}^2, \quad (30)$$

$$b = \omega_{21}^2/\omega_{11}^2 \quad (31)$$

$$c = \omega_{22}^2/\omega_{11}^2 \quad (32)$$

and $$D = c-ab. \quad (33)$$

Equations (24) through (27) were used with two samples A and B to calculate the four parameters required for initial calibration. The results were $\tau_1 = 1.611 \cdot 10^{-8}$ sec, $\tau_2 = 1.805 \cdot 10^{-5}$ sec, $q_1 = 112.42/m$, and $q_2 = 106.92/m$.

Although quantitative data were not obtained it was observed that after about an hour of warm-up time these system parameters would not change sufficiently to deteriorate the precision of thickness measurement.

The value of $\tau_1$ is substantially the lowest that could be obtained by adjusting the trimming capacitor. That for $\tau_2$ is about 7% larger than calculated from the 0.003 $\mu$F capacitor C and the 5.6k collector-resistor $R_c$.

A first approximation for the effective value of the single mode parameter $q$ is the logarithmic slope of the variation of $V_T/V_0$ with transmitter-receiver separation, where $V_0$ is the signal present. Although $q$ was not estimated for the final coils a value of 112/m was obtained with a previous set that were about 1 inch in diameter.

The requirements for making the measurements independent of the axial position of the sample between transmitting and receiving coils were discussed above. An experiment to check this was made at a transmitter-receiver spacing of 7/16 inch. The system was calibrated with two samples A and B initially positioned midway between the coils. Each sample was first displaced +⅛ inch toward the receiver and then −⅛ inch toward the transmitter. The results are shown in Table 4.

Table 4

| | Effect of Sample Position | | | | | |
|---|---|---|---|---|---|---|
| | −⅛″ | | Displacement of Sample $\theta$ | | +⅛″ | |
| | l(mils) | $\sigma$(%) | l | $\sigma$ | l | $\sigma$ |
| A | 8.22 | 35.1 | 8.22 | 35.1 | 8.24 | 35.0 |
| B | 18.56 | 35.0 | 18.57 | 34.9 | 18.60 | 34.8 |

The maximum change in the thickness measurement was less than ¼% and occurred when the sample was displaced toward the receiver by ∼ 30% of the transmitter-receiver separation.

Tests to determine the effects of nearby objects were made. A 6×6 inch A1 sample was approximately centered in all directions with respect to the 2 inch diameter transmitter and receiver coils, which were spaced about one-half inch apart.

Several highly conducting but fixed objects were within 3 to 6 inches of the sensitive region between the transmitter and receiver. These were the A1 clamp that gripped the sample along its lower edge and the two A1 boxes that housed the coil driver and preamplifier. The effects of these if present, were probably included in the calibration.

In one experiment a 6×6×1/16 inch A1 sheet was located with its plane parallel to the coil axis and about one-half inch away from the edge of the sample sheet. The presence of this sheet caused no change in the frequency $f_1$ but the lower frequency $f_2$ changed from 8073 to 8080 Hz. From equation (16) the resulting percentage change in the thickness measurement is + 0.3%.

In another case the head of a pair of small steel cutting pliers was held about one-half inch directly above the receiver coil; $f_1$ changed from 82848 to 83859 and $f_2$ changed from 8073 to 8070. The calculated change in the thickness measurement is 0.2%.

Both experiments were repeated with the sample displaced one-eighth inch toward the receiver and comparable results were again obtained.

When a small brown-paper envelope was inserted between the sample and receiver no frequency changes were observed. With a piece of 1/16 inch thick glass-fiber circuit board in this region by far the largest change was in the lower frequency $f_2$. However, the corresponding thickness error was only 0.2%.

It is concluded that the instrumentation of the present invention is sufficiently insensitive to conducting and magnetic materials near but not within the sensitive transmitter-receiver region and to insulating materials placed within this sensitive region.

High and low closed loop frequencies $f_1$ and $f_2$ were measured for a number of samples. Thickness and conductivity were computed. Results were typically better than ±1%. Further analysis was conducted using five point and six point fits with reduced errors obtained using more samples for calibration.

The significant feature of the apparatus and method just described is that all measurements are transmission measurements. By making all transmission measurements it is possible, as noted above, to use simple coils. Furthermore, accurate measurements are obtained independent of sheet flutter, i.e., the spacing between the transmitter and receiver remains the same despite the position of the sheet. It is a requirement, however, that the impedance of the regions on both sides of the sheet being measured simulate free space. This is accomplished in the transmitter by controlling the current through the coil and in the receiver through the use of a high impedance input to the amplifier stage. This is also the reason, as noted above, that ferrite cores can cause problems.

The method and apparatus described above assume using two frequencies with a single $q$. It should be pointed out that the method of the present invention is not so limited. It is possible to use a single frequency and two $q$'s. It is also possible to use two frequencies and two $q$'s. It will be evident to those skilled in the art that the equations for use in these other variations follow directly from the equations given above.

An alternate method for determining the $I\sigma$ product is to measure the amplitude rather than the phase angle of the sample transmissivity. When the phase angle is 90° the amplitude is $$|T| \propto 2q/(\omega_1 \mu_o l \sigma), \quad (34)$$

where $\omega_1$ is the higher closed-loop frequency.

Referring to FIG. 2 the ratio of the preamplifier output $V_o$ to the coil Driver input $V_i$ will be given by $$V_o/V_i = C \omega_1 |T| \propto 2qC/(\mu_o = \sigma), \quad (35)$$

where $C$ is a constant that can be determined by calibration and depends on the spacing, number of turns, size and shape of the transmitter and receiver coils and on the gains of the Preamplifier and Coil Driver units.

The accuracy of the approximation for $|T|$ is comparable with that of the approximation for the phase angle described above.

The measurement of $|T|$ rather than the lower closed-loop frequency $\omega_2$ will facilitate simultaneous measurement of the two observables required to separate thickness from conductivity.

Thus, an improved thickness gauge using two transmission measurements at different frequencies to obtain inputs for solving two simultaneous equations to determine thickness and conductivity has been shown. Although specific embodiments have been illustrated and described, it will be obvious to those skilled in the art that various modifications may be made without departing from the spirit and the invention which is intended to be limited solely by the appended claims.

What is claimed is:

1. Apparatus for measuring parameters which will permit computing at least one of the thickness and conductivity of a sheet of electrically conductive material without independent information of sheet thickness or sheet conductivity comprising:
    a. a transmitter coil physically located on one side of the sheet to be measured;
    b. means providing an alternating current drive to said transmitter coil;
    c. a receiver coil physically located on the opposite side of said sheet at a fixed distance from said transmitter coil;
    d. a preamplification means having a large input impedance, the input of said means coupled to said receiving coil;
    e. amplifying means having an input from said preamplifying means and providing an input to said means driving said transmitter coil;
    f. means for measuring the frequency of the input to said transmitter driving means, said apparatus being a closed loop system which will oscillate at a frequency determined by the phase shifts within the system;
    g. means in said amplifying means for introducing an additional phase shift into said loop; and
    h. means for selectively inserting said means for introducing an additional phase shift, whereby said system may be operated to take a first measurement with the phase shift within the system determined only by phase shifts without said additional phase shift, resulting in operation at a first frequency and may be operated with said additional phase shift in said system to operate at a different frequency whereby from said phase shifts and measured frequencies, parameters which will permit computing at least one of the thickness and conductivity of said sheet may be determined.

2. Apparatus according to claim 1 and further including automatic gain control means coupling said preamplifier means and said amplifying means obtaining a control output from the output of said amplifying means.

3. Apparatus according to claim 1 wherein said means driving said transmitter coil comprise a transistor in an emitter follower configuration with the coil in the collector circuit of said transistor.

4. Apparatus according to claim 1 wherein the normal phase shift in said system is 90° and said means for introducing an additional phase shift changes the phase shift in said system to approximately 16°.

5. Apparatus for measuring the thickness and conductivity of a sheet of metal comprising:
   a. a transmitter coil physically located on one side of the sheet to be measured;
   b. means to supply alternating current to drive said transmitter coil;
   c. a receiver coil physically located on the opposite side of said sheet at a fixed distance from said transmitter coil;
   d. means to cause said means driving said transmitter coil to operate at a predetermined frequency at which the amplitude and phase angle of the voltage induced by said transmitting coil bear different functional relationships to thickness and conductivity
   e. means to measure the amplitude of the voltage at said transmitter coil;
   f. means to measure, the phase of signal in said receiver coil relative to the phase of signal in said transmitter coil, and the amplitude of the voltage at said receiver coil; and
   g. means to measure the frequency at said transmitter coil.

6. Apparatus as in claim 5 wherein said means to cause, causes said transmitter to operate at a frequency which will result in a relative phase angle between the signals of 90°.

7. A method of measuring parameters which can be used in calculating at least one of the thickness and conductivity of a sheet of electrically conductive material using at least one transmitter coil to induce eddy currents in the sheet and at least one receiver coil to pick up signals responsive to said eddy currents, said measured parameters being such that independent information with respect to sheet thickness and sheet conductivity is not required to calculate the values of at least one of thickness and conductivity comprising:
   a. locating the transmitter coil and receiver coil at a constant spacing from each other on opposite sides of the sheet to be measured; and
   b. making at least two pairs of measurements including:
      1. exciting the transmitter with a first frequency;
      2. measuring said first frequency and the phase of the signal induced in the receiver coil relative to the phase of the signal in the transmitter;
      3. adjusting said first frequency to obtain a relative phase of 90°;
      4. changing the frequency of the transmitter such that the resulting relative phase between said transmitter and said receiver coil signals is approximately 16°, whereby the resulting relative phase will bear a different functional relationship to thickness and conductivity than said first phase measured; and
      5. measuring said relative phase and frequency after said change.

8. A method of measuring parameters which can be used in calculating at least one of the thickness and conductivity of a sheet of electrically conductive material using at least one transmitter coil to induce eddy currents in the sheet and at least one receiver coil to pick up signals responsive to said eddy currents, said measured parameters being such that independent information with respect to sheet thickness and sheet conductivity is not required to calculate the values of at least one of thickness and conductivity comprising:
   a. locating the transmitter coil and receiver coil at a constant spacing from each other on opposite sides of the sheet to be measured; and
   b. making at least two pairs of measurements including:
      1. exciting the transmitter with a first frequency which is near the frequency region where the sheet is thin compared with the calculated skin depth of the eddy currents;
      2. measuring said first frequency and the phase of the signal induced in the receiver coil relative to the phase of the signal in the transmitter;
      3. changing the frequency of the transmitter coil to a frequency region where the thickness of the sheet is approaching the calculated skin depth of the eddy currents;
      4. measuring said relative phase and frequency after said change.

9. A method of measuring parameters which can be used in calculating at least one of the thickness and conductivity of a sheet of electrically conductive material using transmitter coils to induce eddy currents in the sheet and receiver coils to pick up signals responsive to said eddy currents, said measured parameters being such that independent information with respect to sheet thickness and sheet conductivity is not required to calculate the values of at least one of thickness and conductivity comprising:
   a. locating a first transmitter coil and receiver coil at a constant spacing from each other on opposite sides of the sheet to be measured and also locating a second transmitter coil and receiver coil at a constant spacing from each other on opposite sides of the sheet to be measured; and
   b. simultaneously making at least two pairs of measurements including:
      1. simultaneously exciting said first and second transmitters with first and second frequencies which are different and which are such that the relative phase between the signals in the respective first transmitter coil and its associated receiver and the second transmitter coil and its associated receiver coil bear a different functional relationship to thickness and conductivity; and
      2. measuring said first and second frequencies and the phase of the signal at said receiver coils relative to the phase of the signal at said first and second transmitter coils.

* * * * *